United States Patent
Juestel et al.

(10) Patent No.: US 7,901,442 B2
(45) Date of Patent: Mar. 8, 2011

(54) TANNING DEVICE USING SEMICONDUCTOR LIGHT-EMITTING DIODES

(75) Inventors: Thomas Juestel, Witten (DE); Cornelis Reinder Ronda, Aachen (DE)

(73) Assignee: J. W. Holding GmbH, Stuttgart (DE)

( * ) Notice: Subject to any disclaimer, the term of this patent is extended or adjusted under 35 U.S.C. 154(b) by 394 days.

(21) Appl. No.: 10/555,675

(22) PCT Filed: Apr. 27, 2004

(86) PCT No.: PCT/IB2004/050523
§ 371 (c)(1),
(2), (4) Date: Oct. 10, 2006

(87) PCT Pub. No.: WO2004/098709
PCT Pub. Date: Nov. 18, 2004

(65) Prior Publication Data
US 2007/0060985 A1  Mar. 15, 2007

(30) Foreign Application Priority Data

May 9, 2003 (EP) .................................. 03101288

(51) Int. Cl.
*A61N 5/06* (2006.01)
(52) U.S. Cl. .................. 607/91; 607/90; 607/94
(58) Field of Classification Search ............ 607/88–95
See application file for complete search history.

(56) References Cited

U.S. PATENT DOCUMENTS

| 4,469,951 | A | | 9/1984 | Coco et al. |
| 4,600,009 | A | * | 7/1986 | Kramer et al. ............... 607/91 |
| 5,374,825 | A | * | 12/1994 | Doty et al. ................. 250/372 |
| 5,966,393 | A | * | 10/1999 | Hide et al. ................... 372/23 |
| 6,888,303 | B2 | * | 5/2005 | Cameron et al. ........... 313/489 |
| 7,108,712 | B2 | * | 9/2006 | Barghelame ................ 607/91 |
| 7,458,982 | B2 | * | 12/2008 | Kraft et al. ................... 607/88 |
| 2002/0074559 | A1 | * | 6/2002 | Dowling et al. ............ 257/99 |
| 2008/0288032 | A1 | * | 11/2008 | Irwin ........................... 607/94 |

FOREIGN PATENT DOCUMENTS

| DE | 4026327 | | 2/1992 |
| DE | 10116664 | | 10/2002 |
| EP | 1138349 | | 10/2001 |
| EP | 1 839 704 | A1 * | 3/2007 |
| WO | WO2004024234 | | 3/2004 |

OTHER PUBLICATIONS

Schlager et al., "An LED-Array Light Source for Medical Therapy", Proceedings of the SPIE, SPIE, Bellingham, VA, US, vol. 1892, 1993, pp. 26-25, XP000568951.

* cited by examiner

*Primary Examiner* — Ahmed M Farah
(74) *Attorney, Agent, or Firm* — Bacon & Thomas, PLLC

(57) ABSTRACT

A tanning device is described that includes semiconductor light-emitting diodes (LEDs) as a light source, which LEDs are preferably composed of (InGa)N, (AlGa)N, (AlInGa)N or (AlInGa)P as their semiconductor material.

13 Claims, 2 Drawing Sheets

TANNING DEVICE USING SEMICONDUCTOR LIGHT-EMITTING DIODES

The invention relates to the use of semiconductor light-emitting diodes as light sources in a tanning device, e.g., in a sun-bed.

Modern-day tanning devices incorporate low-pressure mercury lamps (TL lamps) and high-pressure mercury lamps (HID lamps). The amount of UVB light is regulated in this case by color filters in the case of the HID lamps and by mixtures of phosphors in the case of the TL lamps. Also, the actual color of the light from the tanning device can be adjusted by using some colored TL lamps. In contrast to this, in accordance with the invention the regulation of the UV radiation and of the color emission is performed by means of light-emitting diodes.

It is known that conventional tanning devices incorporate a combination of low-pressure mercury lamps (TL lamps) and high-pressure mercury lamps (HID lamps). Low-pressure mercury lamps are, for example, used in a sun-bed to irradiate the front of the customer's body and his or her back. High-pressure mercury lamps on the other hand are used only at the top end of the sun-bed, to irradiate the customer's face and head. Both types of lamp emit mainly UVA light, with the amount of UVB radiation being largely determined by the glass of which the lamp is made, which has an absorption edge in the range between 290 and 320 nm. The UVB content of the radiation from low-pressure mercury lamps can also be adjusted by using mixtures of phosphors.

The appearance of the light emitted by a tanning device is largely determined by the visible emission from low-pressure mercury lamps at 405, 436 and 546 nm.

It has now been found that a tanning device has considerable advantages if it also includes light-emitting diodes in which the spectrum of the UV light emitted can be adjusted to suit the customer's wishes.

By using LEDs emitting UVB light, it is possible to overcome the disadvantages that are connected with the use in conventional sun-beds of low-pressure mercury lamps that emit UV light and blue light. Also, the (InGa)N, (AlGa)N or (AlInGa)P LEDs that emit UVB light can be fitted with dimmers to enable the actual spectrum of the UV light from the tanning device to be adjusted to suit the customer's individual wishes. Finally, LEDs that emit visible light can also be used to affect the color of the light emitted. Even white light can be generated in this way, if LEDs emitting yellow or green or red light are used to convert the blue light from the tanning device into white light by additive color mixing. In accordance with the invention, it is possible in this way to produce tanning devices that emit UV radiation in a spectral range between 290 and 320 nm (UVB).

It is, however, also possible for a tanning device to be produced in which the LEDs emit UV light in the spectral range between 320 and 400 nm (UVA).

Finally, it is also possible for a tanning device to be produced in which the LEDs emit light in the range between 400 and 900 nm.

By the use of LEDs, on the one hand the emitted spectrum of the UVB light can be regulated with a dimmer. However, on the other hand color temperature, color rendition and the visible light emitted by the LEDs may also be adjusted with a dimmer.

It is also possible for LEDs emitting infrared light (IR) to be used in the tanning device according to the invention and in this way for the customer to be treated with IR light before the actual tanning operation. There are indications that the application of IR light before irradiation with UV light reduces the adverse effects of the UV light on the human skin.

To ensure uniform distribution within the tanning device, the light from the LEDs may be coupled into a light-conducting sheet made of plexiglass (PMMA) or of some other transparent plastics material, which is fitted to protect the customer in a sun-bed according to the invention (FIGS. 1-3). The light is then coupled out by a covering layer that is applied to the sheet and produces a surface roughness. The diameter of the structures that couple out the light must be in the range of between 100 and 1,000 nm in this case. UV-light can be coupled in a light-conductor of, for example, PMMA, because PMMA is highly transparent up to a wavelength of 280 nm (FIG. 4).

These and other aspects of the invention are elucidated by the accompanying drawings.

In the drawings:

FIG. 1 shows a tanning device according to the invention from the side. It includes a sheet of PMMA acting as a light-guide, from which UV light is coupled out by a rough surface. The light generated by the TL lamps is reflected onto the sheet of PMMA.

Figure 1:
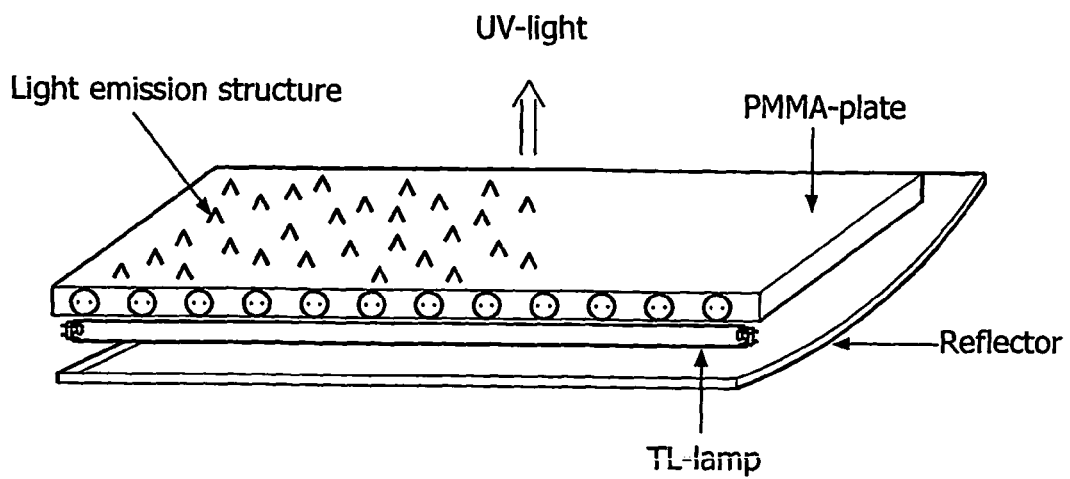
Figure 2:
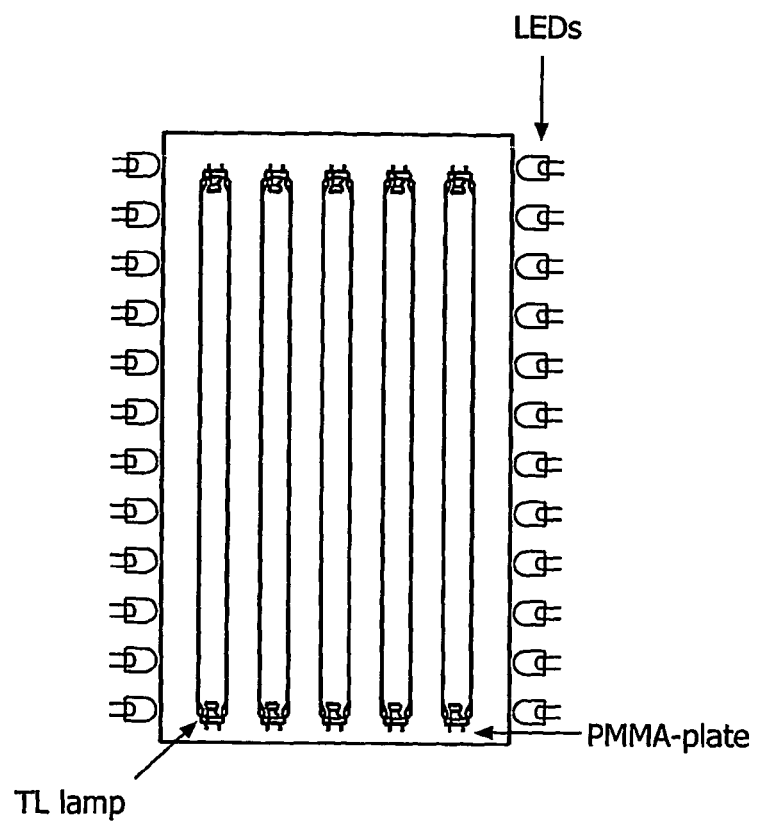
FIG. 2 shows the tanning device according to the invention from above. The TL lamps arranged below the sheet of PMMA can be seen, as also can the LEDs that couple light into the sheet of PMMA from the side.
Figure 3:
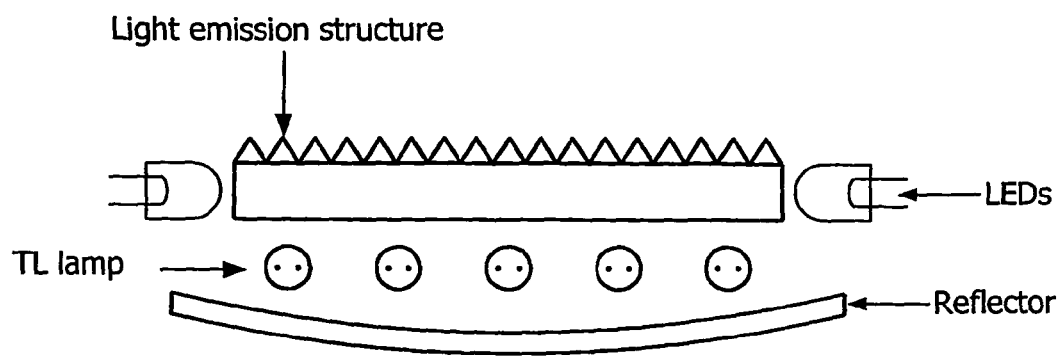
FIG. 3 is a cross-section through the tanning device, of which the TL lamps arranged underneath the sheet of PMMA, the reflector and the LEDs that couple light into the sheet of PMMA laterally can be seen. For coupling-out purposes, the sheet of PMMA is coated with a rough covering layer.
Figure 4:
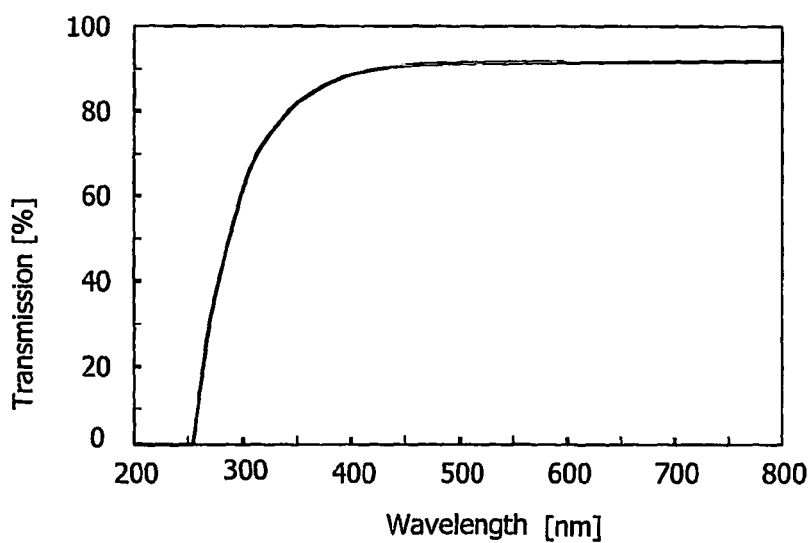
FIG. 4 shows the curve for the transparency of ordinary polymethyl methacrylate at different wavelengths. There is a severe decline in the transparency of the sheet of PMMA to UV light at a wavelength of less than 300 nm.

The invention claimed is:

1. A tanning device, comprising:
    semiconductor light-emitting diodes (LEDs) configured to emit a first light comprising ultraviolet (UV) light;
    low-pressure mercury lamps configured to emit a second light; and
    a light guide arranged to couple in the first light from the LEDs and the second light from the low-pressure mercury lamps and to couple out both of the first and second light as a tanning light of the tanning device, wherein the light guide comprises:
    a first side;
    a second side; and
    a third side, wherein the first side is configured to couple in the first light, wherein the second side is configured to couple in the second light, and wherein the third side is configured to couple out the first and second light together.

2. The tanning device as claimed in claim 1, wherein the LEDs are configured to emit light within a spectral range of 320 to 400 nm.

3. The tanning device as claimed in claim 2, wherein the LEDs emitting UV light are high-energy (InGa)N, (AlGA)N, (AlInGa)N, or (AlInGa)P LEDs.

4. The tanning device as claimed in claim 1, wherein the coupled out first and second light is in the spectral range between 290 and 320 nm (UVB).

5. The tanning device as claimed in claim 1, wherein the LEDs emit light in the spectral range between 400 and 900 nm.

6. The tanning device as claimed in claim 5, comprising a dimmer configured to control the visible light emitted by the LEDs.

7. The tanning device as claimed in claim 1, comprising a dimmer configured to control the color temperature of UVB light emitted by the LEDs.

8. The tanning device as claimed in claim 7, wherein the dimmer controls the color temperature of light emitted by the LEDs to a spectral range of 700 to 900 nm (IRA).

9. The tanning device as claimed in claim 1, wherein the light guide comprises a light conducting sheet configured the UV light and light from the low-pressure mercury lamps together.

10. The tanning device as claimed in claim 9, wherein the light conducting sheet is a polymethyl methacrylate (PMMA) sheet.

11. The tanning device as claimed in claim 9, wherein the second side is arranged opposing the first side, and the third side is arranged substantially perpendicular to the first and second sides.

12. The tanning device as claimed in claim 11, wherein the third side comprises a surface roughness configured to couple out the first and second light together.

13. The tanning device as claimed in claim 12, wherein the surface roughness comprises surface structures having a diameter of the structures that couple out the light in nthe range of between 100 and 1,000 nm.

* * * * *